United States Patent [19]

Tucker

[11] Patent Number: 5,213,574
[45] Date of Patent: May 25, 1993

[54] COMPOSITE IMPLANTABLE BIOCOMPATIBLE VASCULAR ACCESS PORT DEVICE

[75] Inventor: Elton M. Tucker, Medfield, Mass.
[73] Assignee: Device Labs, Inc., Medway, Mass.
[21] Appl. No.: 755,690
[22] Filed: Sep. 6, 1991
[51] Int. Cl.$^5$ .............................................. A61M 11/06
[52] U.S. Cl. ........................................ 604/93; 424/423
[58] Field of Search ............. 424/423; 604/175, 891.1, 604/327, 328, 890.1, 892.1, 93, 181, 256; 128/DIG. 12, 899

[56] References Cited

U.S. PATENT DOCUMENTS

| | | | |
|---|---|---|---|
| 4,673,394 | 6/1987 | Fenton, Jr et al. | 604/175 |
| 4,840,615 | 6/1989 | Hancock et al. | 604/93 |
| 5,041,098 | 8/1991 | Loiterman et al. | 604/175 |

FOREIGN PATENT DOCUMENTS 0258777  3/1988  European Pat. Off. ......... 604/891.1

Primary Examiner—Thurman K. Page
Assistant Examiner—Carlos Azpuru
Attorney, Agent, or Firm—Samuels, Gauthier & Stevens

[57] ABSTRACT

A composite implantable biocompatible vascular access port device for delivering a fluid medication to or withdrawing a fluid medication from the body. The device has a non-metallic housing defining an interior chamber with inlet and outlet openings, a self-sealing penetrable septum, a metallic chamber liner, and a metallic delivery conduit. The septum closes the inlet opening and provides a seal through which fluids may be injected into or withdrawn from the chamber. The metallic chamber liner underlies and seals against the septum and cooperates with it to isolate the injected fluid medication from the housing and from leakage into body tissue. The metallic delivery conduit communicates with the interior of the liner, and extends through the outlet opening to convey fluid medication to the exterior of the housing.

18 Claims, 1 Drawing Sheet

COMPOSITE IMPLANTABLE BIOCOMPATIBLE VASCULAR ACCESS PORT DEVICE

BACKGROUND OF THE INVENTION

The invention relates to implantable biocompatible vascular access port devices used in the delivery of medicines, treatments, or any other fluids into a body and/or the withdrawal of fluids from the body.

Access port devices are surgically implanted under the skin and generally include an outlet opening connected by means of a tubular conduit (catheter) system to a blood vessel within the body. Typically, such devices include septums which serve as covers for the medicine chambers and are comprised of materials which automatically reseal themselves after having been penetrated by a hypodermic needle. Fluid medications are typically infused via hypodermic needles attached to a syringe. The needle passes through the skin and through the septum into the chamber, allowing the fluid to be injected into the chamber and expelled through the catheter into the selected body site.

Conventional access port devices have either all-plastic or all-metal constructions. The plastic constructions are advantageous in that they are inexpensive to fabricate utilizing conventional molding techniques. However, plastic constructions have the disadvantage that fluids being infused into a patient sometimes react with the material and leach out unwanted or harmful compounds from the plastic material in the fluids being infused. For example, polyethersulfone is a material commonly used in such all-plastic devices. Substances found to be incompatible with polyethersulfone are acetaldehyde, aniline, benzaldehyde, chlorobenzene, chloroform, phenol, pyridine, and toluene.

Plastic constructions also have the drawback that certain compounds from the fluids sometimes adhere to the plastic reservoir surfaces, and in so doing result in an undesirable reduction or change of the potency of the fluid being delivered to the patient.

All-metal constructions significantly increase implant weight, are limited in possible design shapes, and are labor intensive to manufacture. In some cases, the metal structures are enveloped with a silastic rubber coating to improve the exterior surface and to make the device softer and more desirable for implantation and tissue contact. Such surface coatings, however, fail to address the basic shortcomings of all-metal structures and in some cases may create new hazards.

There is a need therefore for an access port device which has non-reactive metallic surfaces in contact with the fluid medications, is similar in weight to the all-plastic devices, and is easy to manufacture.

With the foregoing in mind the object of the invention is to provide a composite structure which takes advantage of the low cost, high quality construction methods available through the use of molded plastic materials, and which also takes advantage of the non-reactive characteristics of certain metallic surfaces.

SUMMARY OF THE INVENTION

The invention relates to a non-reactive, implantable, biocompatible vascular access port device for delivering or withdrawing a fluid or medication. The device has a non-metallic housing defining an interior chamber with inlet and outlet openings, a self-sealing penetrable septum, a metallic chamber liner, and a metallic delivery conduit.

The septum closes the inlet opening and provides a seal through which fluid medication may be injected into the chamber. The metallic chamber liner underlies and cooperates with the septum to isolate the injected fluid medication from the housing. The metallic conduit communicates with the interior of the liner, and extends through the outlet opening to convey fluid medication to the exterior of the housing.

The device is non-reactive because the injected fluid medication is isolated from the housing and is in contact with only the non-reactive septum and the non-reactive metallic surfaces of the chamber liner and delivery conduit. The metallic chamber liner confines the fluid medication after it is introduced through the septum. The metallic chamber liner is sealed against the septum so that fluids cannot escape from the chamber except through the metallic delivery conduit. The delivery conduit is in turn coupled externally to a delivery system, which typically includes a catheter.

BRIEF DESCRIPTION OF THE DRAWINGS

Other features and objects of the invention are further illustrated in the accompanying drawings in which.

DETAILED DESCRIPTION OF THE PREFERRED EMBODIMENT

Figure 1:
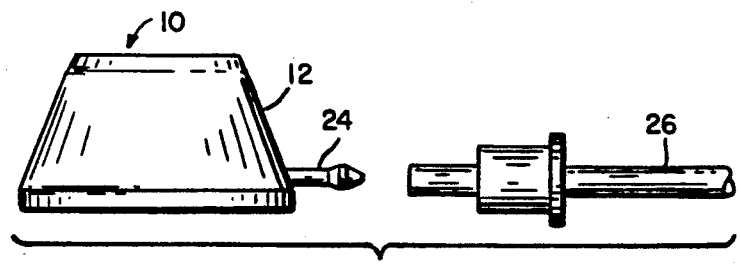
FIG. 1 is a side view of an access port device according to the present invention shown coupled from an associated catheter.
Figure 2:
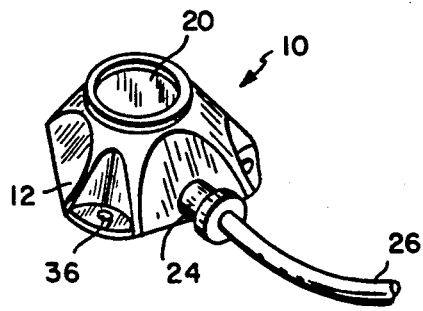
FIG. 2 is an assembled perspective view of the components shown in FIG. 1.
Figure 3:
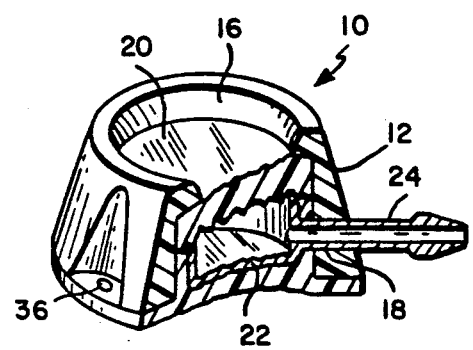
FIG. 3 is a cut-away view of the access port device.

FIGS. 1-4 illustrate an access port device 10 for delivering fluid medication according to the present invention. Access port device 10 includes non-metallic housing 12 defining interior chamber area 14 with inlet and outlet openings 16, 18 communicating therewith; a self-sealing penetrable septum 20; a metallic chamber liner 22; and a metallic delivery conduit 24.

Figure 4:
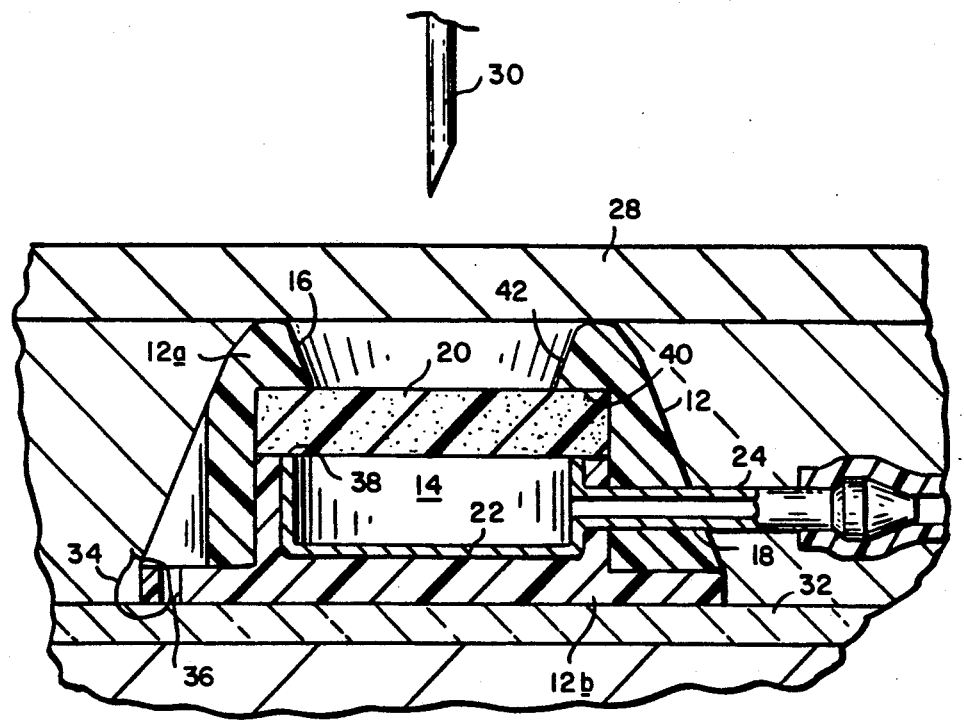
FIG. 4 is a cross-sectional view of the access port device as implanted according to the present invention.

The self-sealing penetrable septum 20 closes inlet opening 16 and provides a medium through which fluid medication may be injected into interior chamber area 14. Metallic chamber liner 22 underlies septum 20 and cooperates with it to isolate injected fluid medication from housing 12. Metallic delivery conduit 24 communicates with the interior of metallic chamber liner 22 and extends through outlet opening 18 to convey fluid medication to or from the exterior of housing 12. The delivery conduit 24 is suitably adapted for connection to a catheter 26 or other like conventional external delivery component. As shown in FIG. 4, the access port device 10 of the present invention is designed to be surgically implanted under the skin 28.

Septum 20 ma be fabricated of any known "self-sealing" material such as silicone rubber. The septum automatically reseals itself after having been penetrated by the needle 30 of a syringe. Fluid medications are injected via hypodermic needles through the skin 28 and septum 20 into the chamber area 14. Typically, the device 10 is secured to fascia 32 underlying the skin 28 by means of sutures 34 threaded through peripheral apertures 36.

Metallic chamber liner 22 is in sealed communication with septum 20 such that fluid medications injected into chamber area 14 come in contact with only septum 20, metallic chamber liner 22, and metallic delivery conduit 24. Metallic chamber liner 22 and metallic delivery conduit 24 are constructed of any known non-reactive material such as titanium or high grade stainless steel.

Housing 12 may be subdivided into upper and lower segments 12a, 12b, each being molded of any biocompatible non-metallic material such as for example, polyethersulfone. Metallic chamber liner 22 sits inside interior chamber area 14 and in effect serves as a reservoir cup for the fluid medication. During assembly, the upper and lower housing segments 12a, 12b, are assembled together, for example by being bonded, screwed, pinned, snapped, etc. with the septum 20 and liner 22 captured therebetween. The upper rim 38 of the liner is in tight sealing engagement with the underside or circumference of the septum, the latter in turn being in tight sealing engagement as at 40 with the underside of an inwardly projecting rim 42 surrounding the inlet opening 16. Alternatively, access port device 10 may be integrally molded around the septum 20 and the metallic chamber liner 22 and metallic delivery conduit 24.

The composite construction of the present invention takes advantage of the low-cost, high quality production methods made possible through the use of molded, light weight, plastic materials, and non-reactive characteristics of selected metals, preferably titanium, stainless steel and the like.

The resulting composite structure of the invention is high in strength, light in weight, biocompatible, and provides non-reactive surfaces for fluids and medications. The composite device can be produced at a lower cost than all-metal devices, without sacrificing the non-reactive features of such metal devices.

I claim:

1. A surgically implantable device for delivering a fluid medication to a body, said device comprising:
    housing means of a biocompatible non-metallic first material defining an interior chamber with communicating inlet and outlet openings;
    a unitary cup-shaped element of a metallic second material compatible with said fluid medication and received in and lining the interior surface of said chamber;
    self-sealing septum means closing said inlet opening and through which said fluid medication may be injected into said chamber;
    said cup-shaped element cooperating in sealing engagement with said septum means to isolate the thus injected fluid medication from contact with said first material of said housing; and
    conduit means communicating with said cup-shaped element and extending through said outlet opening to discharge fluid medication from said chamber to the exterior of said housing.

2. The device as claimed in claim 1, wherein said first material is plastic.

3. The device as claimed in claim 1, wherein said first material is polyethersulfone.

4. The device as claimed in claim 1, wherein said first material is elastomeric.

5. The device as claimed in claim 1, wherein said second material is stainless steel.

6. The device as claimed in claim 1, wherein said second material is titanium.

7. The device as claimed in claim 1, wherein said housing is molded around said cup-shaped element during fabrication.

8. The device as claimed in claim 1, wherein said housing comprises an upper housing portion and a lower housing portion, wherein said upper housing portion and said lower housing portion are assembled together around the cup-shaped element during fabrication.

9. A surgically implantable device for delivering a fluid medication to or withdrawing a body fluid from a body, said device comprising:
    a biocompatible non-metallic housing defining an interior chamber and inlet and outlet openings communicating with said chamber;
    a metallic unitary cup-shaped element compatible with said fluids and received in and lining the interior surface of said chamber;
    a self-sealing penetrable septum closing said inlet opening and providing a means through which said fluids may be injected into or removed from said chamber;
    said cup-shaped element cooperating in sealing engagement with said septum means to isolate said fluids from said housing; and
    a metallic conduit communicating with the cup-shaped element, and extending through said outlet opening for conveying said fluids into and out of said housing.

10. The device as claimed in claim 9, wherein said non-metallic housing is made of plastic.

11. The device as claimed in claim 9, wherein said non-metallic housing is made of polyethersulfone.

12. The device as claimed in claim 9, wherein said non-metallic housing is made of an elastomeric material.

13. The device as claimed in claim 9, wherein said metallic cup-shaped element is made of stainless steel.

14. The device as claimed in claim 9, wherein said metallic cup-shaped element is made of titanium.

15. The device as claimed in claim 9, wherein said metallic conduit is made of stainless steel.

16. The device as claimed in claim 9, wherein said metallic conduit is made of titanium.

17. The device as claimed in claim 9, wherein said non-metallic housing is molded around said metallic cup-shaped element during fabrication.

18. The device as claimed in claim 9, wherein said non-metallic housing comprises an upper housing portion and a lower housing portion wherein said upper housing portion and said lower housing portion are assembled together around the metallic cup-shaped element during fabrication.

* * * * *